United States Patent [19]

Gerson et al.

[11] Patent Number: 5,013,751

[45] Date of Patent: May 7, 1991

[54] (+) SUPROFEN ESTERS AND AMIDES AS OPTHALMIC ANTI-INFLAMMATORY AGENTS

[75] Inventors: Steven H. Gerson; Wesley W. Han, both of Fort Worth, Tex.

[73] Assignee: Alcon Laboratories, Inc., Fort Worth, Tex.

[21] Appl. No.: 573,516

[22] Filed: Aug. 27, 1990

Related U.S. Application Data

[63] Continuation of Ser. No. 463,066, Jan. 10, 1989, abandoned, which is a continuation of Ser. No. 358,473, May 30, 1989, abandoned, which is a continuation of Ser. No. 249,624, Sep. 26, 1988, abandoned, which is a continuation of Ser. No. 948,181, Dec. 31, 1986, abandoned.

[51] Int. Cl.$^5$ .................... A61K 31/38; C07D 333/22
[52] U.S. Cl. ...................................... 514/448; 549/72
[58] Field of Search ........................ 514/448; 549/72

[56] References Cited

U.S. PATENT DOCUMENTS

| | | | |
|---|---|---|---|
| 4,159,986 | 7/1979 | Clemence | 549/72 |
| 4,559,343 | 12/1985 | Han et al. | 549/72 |

FOREIGN PATENT DOCUMENTS

| | | | |
|---|---|---|---|
| 2211214 | 3/1972 | Fed. Rep. of Germany | 549/72 |
| 0203011 | 6/1981 | Japan | 514/448 |

OTHER PUBLICATIONS

Van Daele, P. G. H. et al., *Arzneim-Forsch* (Drug-Res.), 25(10):1495 (1975).

*Primary Examiner*—Alan Siegel
*Attorney, Agent, or Firm*—James A. Arno; Sally S. Yeager; Julie J. L. Cheng

[57] ABSTRACT

Disclosed are esters and amides of (+) suprofen, substantially free of the corresponding enantiomorp, (−) suprofen, having enhanced delivery characteristics on topical administration to the eye; also disclosed are pharmaceutical compositions comprising such (+) suprofen derivatives and methods of using them when indicated to achieve an anti-inflammatory effect on topical delivery to the eye.

8 Claims, No Drawings

(+) SUPROFEN ESTERS AND AMIDES AS OPTHALMIC ANTI-INFLAMMATORY AGENTS

This is a continuation of application Ser. No. 463,066, filed Jan. 10, 1989 now abandoned, which is a continuation of Ser. No. 358,473, filed May 30, 1989 (now abandoned) which is a continuation of Ser. No. 249,624 filed Sept. 26, 1988 (now abandoned) which is a continuation of Ser. No. 948,181 filed Dec. 31, 1986 (now abandoned).

BACKGROUND OF THE INVENTION

This invention relates to certain esters and amides of (+) suprofen having enhanced delivery characteristics on topical administration to the eye. This invention also relates to pharmaceutical compositions comprising such suprofen derivatives and to methods of using them when indicated to achieve an anti-inflammatory effect on topical delivery to the eye.

U.S. Pat. No. 4,559,343, issued Dec. 12, 1985, discloses pharmaceutical compositions and methods of treatment employing various known, nonsteroidal analgesic/anti-inflammatory agents, including racemic suprofen. To the extent that this patent teaches tha ophthalmic pharmacology of racemic suprofen, it is incorporated herein by reference since such disclosure can be applied with efficiency in teaching the pharmaceutical compositions and methods of treatment employing the (+) suprofen esters and amides of the present invention. However, as is disclosed in U.S. Pat. No. 4,559,343, suprofen per se at appropriate dosage concentrations for ophthalmic delivery is generally perceived as stinging. Thus, it was the purpose of the disclosed and claimed invention in U.S. Pat. No. 4,559,343 to define formulations which tend to decrease the stinging sensation associated with the application of racemic suprofen to the eye. The pharmaceutical compositions and methods of treatment of U.S. Pat. No. 4,559,343 employ a complex of suprofen and a xanthine derivative, such as, caffeine to achieve the stated objective. The consensus of the clinical experience involving the disclosed xanthine-suprofen compositions of U.S. Pat. No. 4,559,343, however, is that the alleged comfort formulation is only moderately improved. And this is particularly true in situations wherein the exquisitely sensitive cornea is rendered even more sensitive through comprised health or trauma.

Unexpectedly, it has been discovered that substantially all (ca. 70-fold) of the ophthalmic anti-inflammatory activity of racemic suprofen resides in its (+) enantiomorph. Further, ophthalmic formulations comprising (+) suprofen substantially free of (−) suprofen and at concentration level of approximately one-half of the prior recommendations for the racemic mixture are equivalent in efficacy to such prior art formulations; and further such formulations may be employed at this one-half strength level without the acute stinging sensation which attends the use of full strength formulations of racemic suprofen. Such isomeric effect is also seen for the (+) suprofen esters and amides of the present invention.

The expression, relative to the purity of (+) suprofen compounds, that it be "substantially free of (−) suprofen" means that the corresponding (−) suprofen enantiomorph is co-present is such mixtures at a concentration level of from 0 to 5%. Preparations of such substantially pure forms of (+) suprofen for starting material in preparing the esters and amides of the present invention can be achieved by stereo-selective synthesis, or (+) suprofen can be isolated from the racemic mixture by conventional methods, such as, forming diastereoisomeric salts with optically active organic amines, for example, alpha-methylbenzylamine, which, in fact, is a published accomplishment. Reference is made to U.S. patent application Ser. No. 933,840, filed Nov. 24, 1986 entitled *Ophthalmic Anti-Inflammatory Compositions Comprising (+) Suprofen*, which application is incorporated herein by reference.

Suprofen, alpha-methyl-4-[2-thienylcarbonyl] benzeneacetic acid, is an inhibitor of prostaglandin biosynthesis with analgesic, antipurretic and anti-inflammatory properties. Suprofen was developed by Janssen Pharmaceutica; Beerse, Belgium, as disclosed in P. G. H. Van Daele, J. M. Boey, V. K. Sipido, M. F. L. De Bruyn, and P. A. J. Janssen; *Arzneim-Forsch*, (Drug Res.), 25 (10), 1495 (1975). This article is incorporated herein by reference to the extent that it teaches the preparation of suprofen and techniques of synthesis of certain esters and amides of suprofen which are described in that article, and which techniques, by analogy, provide an enabling disclosure on how to prepare the compounds of the present invention. The esters and amides of (+) suprofen of the present invention are not disclosed by the incorporated by reference article and further the species disclosed in the prior art do not possess an attribute unique to the (+) suprofen species of the present invention which property relates to their ability to be transported across the cornea and thus made available for the ophthalmic anti-inflammatory effect when administered to the eye. Beyond the disclosed original article relating to suprofen esters and amides, there appears to be no relevant prior art relating to suprofen derivatives and the ability of such suprofen species to be transported across the cornea for purposes of enhancing drug delivery. Cross reference, however, is made to applicants' co-pending, concurrently filed, commonly assigned U.S. patent application Ser. No. 06/948,184 also entitled Suprofen Esters and Amides as Ophalmic Anti-Inflammatory Agents.

DETAILED DESCRIPTION OF THE INVENTION

The (+) suprofen esters and amides of the invention may be described by the following formula:

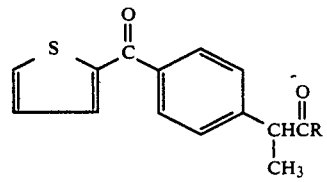

wherein R is selected from the group consisting of alkoxyl and hydroxyalkoxyl of 3 to 8 carbon atoms and alkylamino of 3 to 8 carbon atoms. Especially preferred values for R include:

—OCH₂CH₂OH

—OCH₂CH₂CH₂OH

—OCH₂CH₂CH₂CH₂CH₂OH

—OCH₂CH₃

—OCH$_2$CH$_2$CH$_3$

—OCH$_2$CH$_2$CH$_2$CH$_2$CH$_2$CH$_3$

—OCH(CH$_2$CH$_3$)$_2$

—NHCH$_2$CH$_2$CH$_2$CH$_3$

—OCH(CH$_3$)(CH$_2$CH$_3$)

It has been found that when ocular inflammation is treated using the compounds and compositions of the present invention, that improved bioavailability is achieved as compared to suprofen.

The compound of formula (I) are produced conventionally by reaction of stoichiometric amounts of (+) suprofen and the appropriate alkane diol in an acid solution, preferably an HCl solution. The amides are formed by reaction of (+) suprofen with the appropriate amine by known methods.

The following description is presented to illustrate the method of synthesis. The following procedure may be used to prepare all esters of (+) suprofen (I):

A solution of 0.5 g (+) suprofen, 0.5 mL of concentrated hydrochloric acid, and 10 mL of the appropriate alcohol are heated at 100° C. for 16 hours. The reaction mixture is allowed to cool to 22° C., and is then poured into a separatory funnel containing 20 mL of chloroform and 20 mL of 5% Na$_2$CO$_3$. The organic layer is separated and washed three times with 1N NaOH and three times with distilled water and then dried over magnesium sulfate. Evaporation of solvent gives the appropriate ester, which is purified by chromatography (30 g silica gel; 50% hexane, 50% ethylacetate).

(+Suprofen 1-butyl amide may be prepared as follows:

To a solution of 0.50 g (0.00192 mole) (+) suprofen, 0.28 g (0.00384 mole) n-butylamine, and 0.39 g (0.00384 mole) triethylamine in 100 mL methylene chloride is added 0.40 g (0.00192 mole) dicyclohexylcarbondiimide. The reaction mixture is stirred at 22° C. for 48 hours, after which time the formed dicyclophexylurea is removed by filtration. The organic solution is washed three times with 0.1N NaOH, and three times with distilled water, and dried over magnesium sulfate. The solvent is removed by evaporation, and the product which is obtained is isolated from ethyl acetate.

The preparation of other (+) suprofen amides of structure I follows by analogy when an appropriate amount of the chosen amine is taken in substitution for the above illustrated 1-butyl amine.

Consistent with the teachings of the incorporated by reference U.S. Pat. No. 4,559,343, the ophthalmic anti-inflammatory derivatives of (+) suprofen (I) can be used with the xanthine derivatives, and a representative formulation exemplifying the xanthine of choice, caffeine, which is given below. In the alternative, pharmaceutical compositions comprising (+) suprofen derivatives (I) in aqueous solution, optionally containing a preservation for multidose use and other conventionally employed ophthalmic adjuvants, including a salt entity to adjust the tonicity of solutions, can be employed. The most preferred form of delivery is by eye drops; however, formulations wherein the final specialty form is a gel or ointment can also be employed and formulated according to conventional technology. The ophthalmic compositions of the present invention will typically contain one or more compounds of formula (I) in an amount of from about 0.05% to about 2.0 wt. %, preferably from about 0.1% to about 1.5% wt. %.

A particularly preferred aqueous vehicle for the compounds of formula (I) is one comprising 0.5% to 3.0% wt. % of a polyoxypropylene surfactant having polyoxyethylene groups at either end. These surfactants are known commercially as pluronics. PLURONIC P-84 is particularly preferred. The presence of such surfactants accentuates the bioavailability and desired pharmacological effect of the present (+) suprofen derivatives of formula (I).

Further, additional therapeutic agents including steriods, such as, dexamethasone; antibiotics, such as gentamicin; anti-infectives, such as, sulfonamides; and antiallergics, such as, antihistamines, may be added to and supplement the ophthalmic compositions of the present invention.

The compositions may contain preservatives such as thimerosal, chlorobutanol, benzalkonium chloride, Onamer M, or chlorhexidine; buffering agents, such as phosphates, borates, carbonates and citrates; and thickening agents, such as, high molecular weight carboxy vinyl polymers, such as, the ones sold under the name of Carbopol which is a trademark of the B. F. Goodrich Chemical Company, hydroxyethylcellulose, or polyvinyl alcohol, for example.

The compositions are prepared by dissolving the various ingredients in the required amount of water with stirring to ensure that all the ingredients are dissolved. The aqueous compositions of the invention may be solutions, suspensions, or gels. After preparation of the solution, suspension, or gel the compositions are then packaged in dispensers suitable for delivery of the ophthalmic composition.

The following examples of ophthalmic compositions typify the manner in which the invention may be practiced. The examples should be construed as illustrative, and not as a limitation upon the overall scope of the invention. The percentages are expressed on a weight-/volume basis.

| Ingredient | Concentration (w/v %) |
| --- | --- |
| (+) suprofen pentanediol ester | 0.7% |
| Pluronic P-84 | 1.0% |
| Benzalkonium Chloride | 0.01 + 10% excess |
| Disodium Edetate | 0.1% |
| Dried Sodium Phosphate | 0.1% |
| Sodium biphosphate | 0.03% |
| Sodium Chloride | 0.6% |
| pH adjustment with NaOH or HCl | q.s. pH 7.4 |
| Purified Water | q.s. 100% |

| Ingredient | Concentration (w/v %) |
| --- | --- |
| (+) suprofen propandiol ester | 0.7% |
| Caffeine | 1.0% |
| Pluronic P-84 | 1.0% |
| Benzalkonium Chloride | 0.01 + 10% excess |
| Disodium Edetate | 0.1% |
| Dried Sodium Phosphate | 0.1% |
| Sodium biphosphate | 0.03% |
| Sodium Chloride | 0.6% |
| pH adjustment with NaOH or HCl | q.s. pH 7.4 |
| Purified Water | q.s. 100% |

As noted above the preferred mode of delivery is by eye drops. The frequency of daily dosing and the duration of treatment are left to the routine discretion of the clinician when indicated for an ophthalmic anti-inflammatory effect.

It should be understood that while certain preferred embodiments of the present invention have been illustrated and described, various modifications thereof will become apparent to those skilled in the art. Accordingly, the scope of the present invention should be defined by the appended claims and equivalents thereof.

Various features of the invention are set forth in the following claims.

What is claimed is:

1. A compound of the following formula:

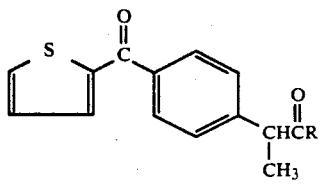

wherein R is selected from the group consisting of alkoxyl and hydroxyalkoxyl of 3 to 8 carbon atoms and alkylamino of 3 to 8 carbon atoms, wherein the remaining moiety attached to R is (+) suprofen substantially free of (−) suprofen.

2. A compound according to claim 1 which is the pentanediol ester of (+) suprofen.

3. A compound according to claim 1 which is the butylamine amide of (+) suprofen.

4. An ophthalmic, anti-inflammatory composition for topical application to the eye comprising a therapeutically effective amount of a compound according to claim 1.

5. An ophthalmic, anti-inflammatory composition for topical application to the eye comprising an aqueous solution containing from about 0.05% to about 2.0% by weight of an amide or ester of (+) suprofen substantially free of the corresponding (−) suprofen species.

6. A composition according to claim 5 wherein the ester or amide is the pentanediol ester or butylamine amide.

7. A method for the treatment of ophthalmic inflammation which comprises administration of a composition of claim 5.

8. A method according to claim 7 wherein the ester or amide is the pentanediol ester or butylamine amide.

* * * * *